United States Patent [19]

Bunce et al.

[11] Patent Number: 5,540,888
[45] Date of Patent: Jul. 30, 1996

[54] LIQUID TRANSFER ASSAY DEVICES

[75] Inventors: Roger A. Bunce, Kings Norton; Stephen J. Starsmore, Selly Oak, both of England

[73] Assignee: British Technology Group Limited, London, England

[21] Appl. No.: 477,263

[22] Filed: Jun. 7, 1995

Related U.S. Application Data

[63] Continuation of Ser. No. 211,494, Apr. 7, 1994, abandoned, which is a continuation-in-part of Ser. No. 961,542, Oct. 15, 1992, Pat. No. 5,354,538.

[30] Foreign Application Priority Data

Nov. 11, 1991 [GB] United Kingdom .................. 9123903

[51] Int. Cl.⁶ .................................................. G01N 30/00
[52] U.S. Cl. ........................ 422/100; 422/103; 422/58; 436/169; 436/170
[58] Field of Search ................................ 422/55–60, 99, 422/100, 102, 103; 436/169, 170, 180, 810

[56] References Cited

U.S. PATENT DOCUMENTS

| | | | |
|---|---|---|---|
| 3,620,677 | 11/1971 | Morison | 23/253 |
| 3,799,742 | 3/1974 | Coleman | 23/253 R |
| 4,756,884 | 7/1988 | Hillman et al. | 422/73 |
| 4,849,340 | 7/1989 | Oberhardt | 435/13 |
| 4,861,711 | 8/1989 | Friesen et al. | 436/7 |
| 4,946,795 | 8/1990 | Gibbons et al. | 436/179 |
| 5,198,193 | 3/1993 | Bunce et al. | 422/100 |
| 5,260,221 | 11/1993 | Ramel et al. | 436/169 |

FOREIGN PATENT DOCUMENTS

| | | |
|---|---|---|
| WO89/03992 | 10/1988 | WIPO. |
| WO90/11519 | 3/1990 | WIPO. |
| WO91/02589 | 8/1990 | WIPO. |
| WO93/10457 | 11/1992 | WIPO. |

*Primary Examiner*—Jill Warden
*Assistant Examiner*—Long V. Le
*Attorney, Agent, or Firm*—Nixon & Vanderhye

[57] ABSTRACT

The present invention relates to a device for performing biochemical diagnostic assays. The device, which is preferably provided in a self-contained disposable form for use in extra-laboratory conditions, comprises two liquid flow channels of porous material which transfer liquid by capillary flow to a common site in sequentially timed manner following simultaneous application of the liquid to the ends of the channels. The channels interconnect at a certain point and then both continue in an arrangement analogous to an electrical bridge circuit. By selecting the hydraulic resistances of the arms of this circuit the flow can be controlled across the bridge. Balancing the circuit will produce null flow across the bridge and prevent the flow from one channel from dominating that from the other when the channels are saturated. Alternatively the arrangement can be such as to produce oscillating flow across the interconnection.

17 Claims, 3 Drawing Sheets

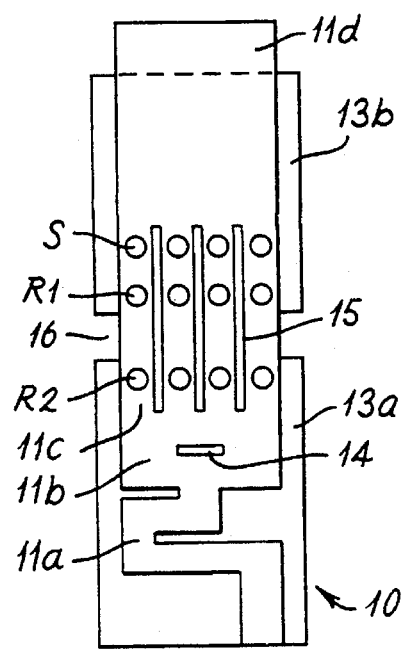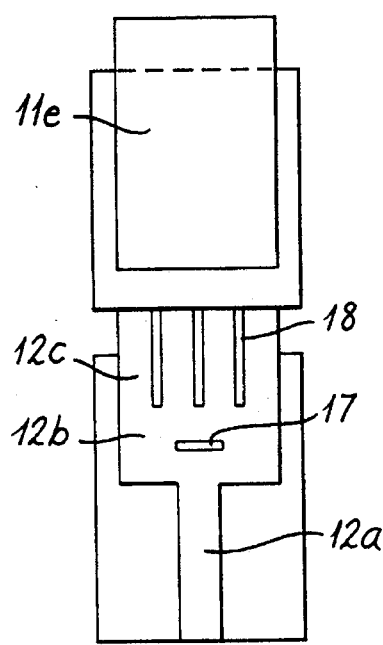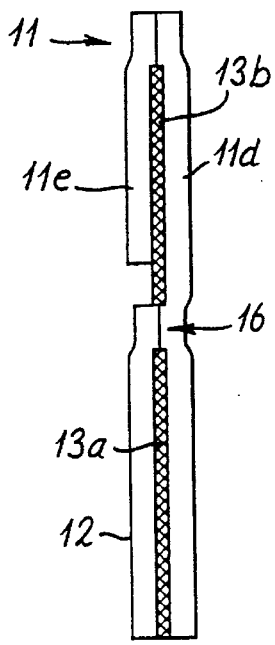
Fig.1a    Fig.1b    Fig.1c
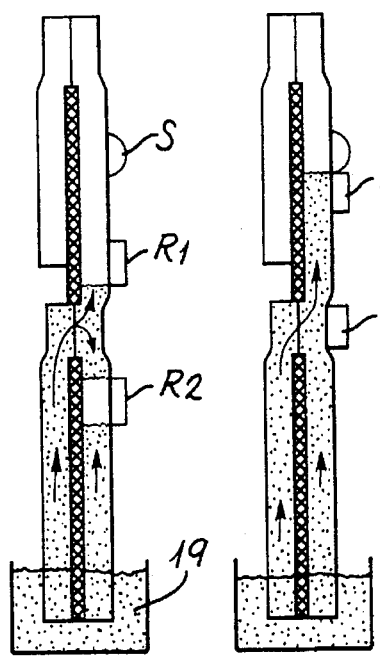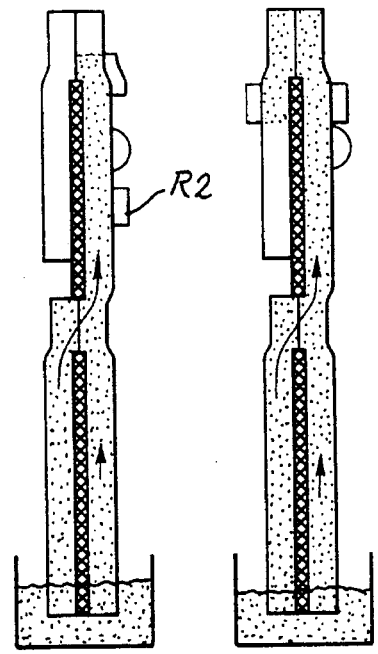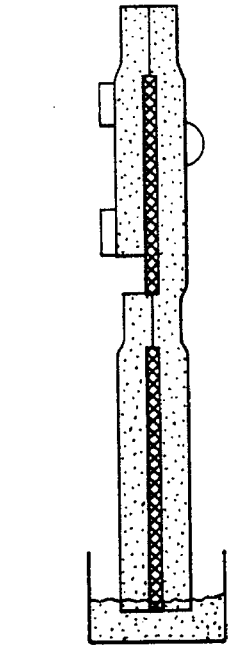
Fig.1d    Fig.1e    Fig.1f    Fig.1g    Fig.1h

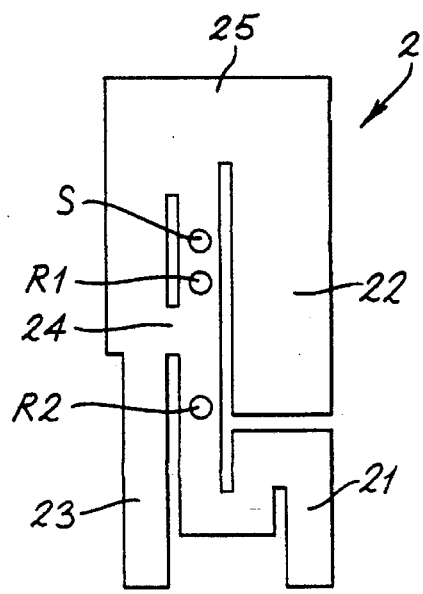
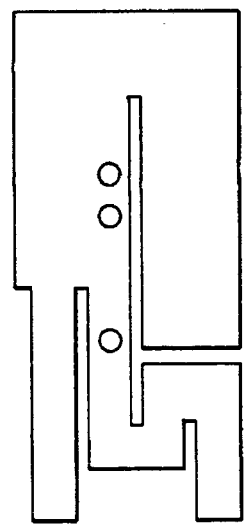
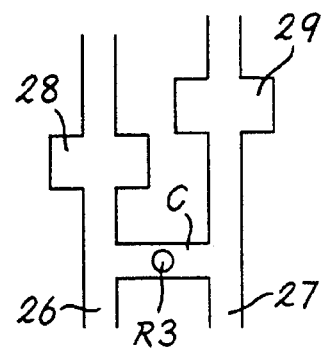
Fig.2a   Fig.2b   Fig.2c
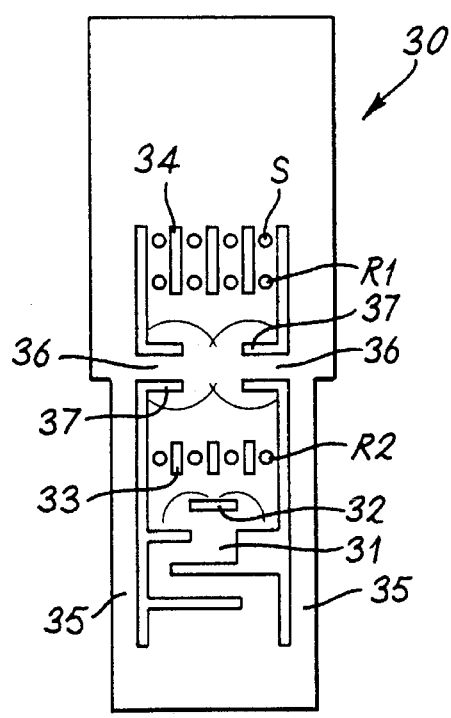
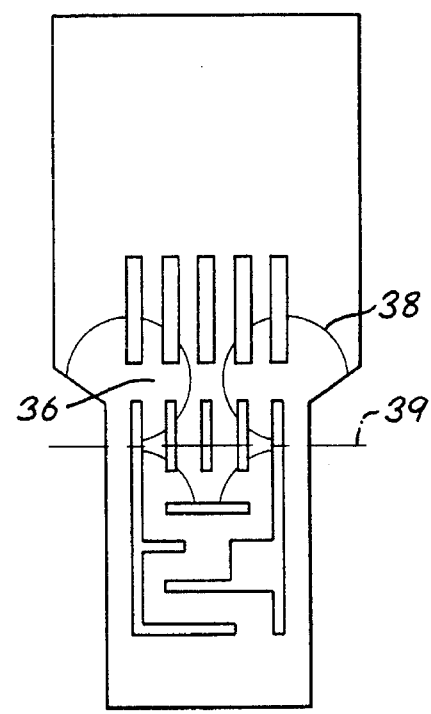
Fig.3a   Fig.3b

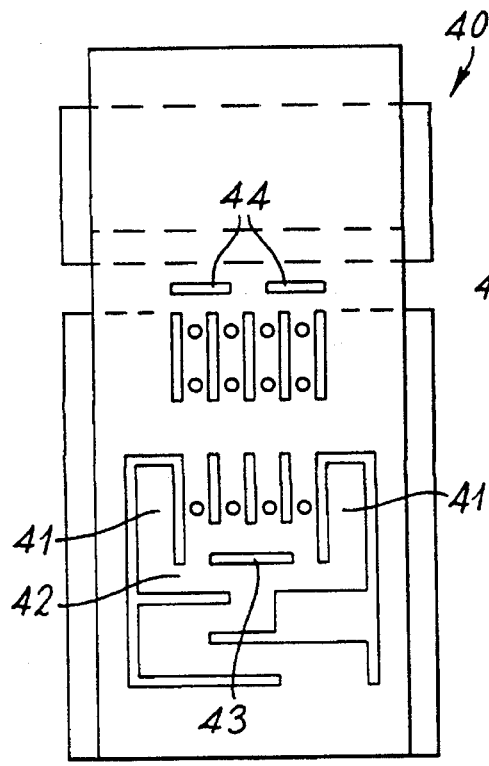
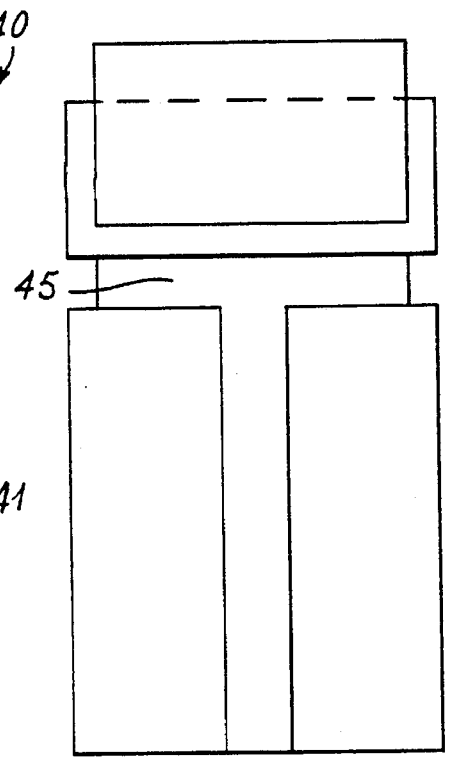
Fig.4a     Fig.4b     Fig.4c
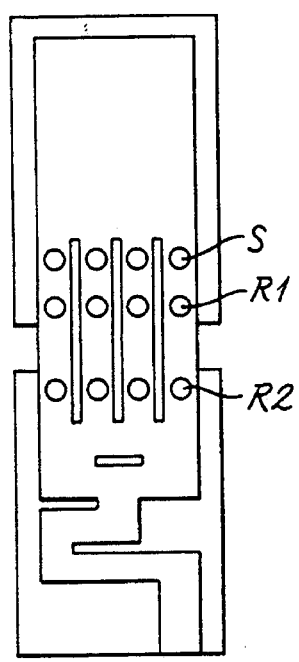
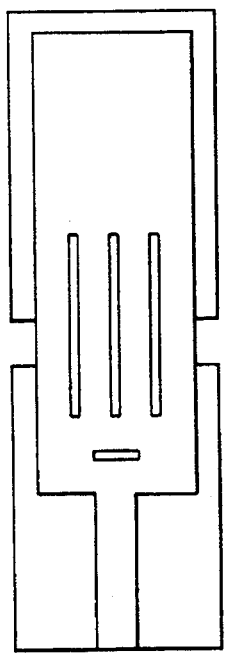
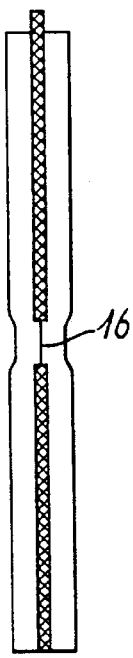
Fig.5a     Fig.5b     Fig.5c

LIQUID TRANSFER ASSAY DEVICES

This application is a continuation of application Ser. No. 08/211,494, filed Apr. 7, 1994, now abandoned which is a continuation-in-part of application Ser. No. 07/961,542, filed Oct. 15, 1992, now U.S. Pat. No. 5,354,538.

There is considerable commercial interest in simple, disposable, self-contained devices for performing biochemical diagnostic assays in extra-laboratory situations. Ideally such devices should avoid any need for complex manual procedures, such as a timed sequence of reagent additions to an analyte, and so be suitable for use by lay persons.

BACKGROUND OF THE INVENTION

According to Patent Specification WO90/11519 such devices can be of a kind comprising first and second liquid flow channels of porous materials leading from a respective pair of channel ends to a common site, which channels are operable to transfer liquid by capillary flow to the common site in sequentially timed manner following simultaneous application of the liquid to the pair of channel ends.

In one more particular form of this kind of device the first and second channels merge into, and transfer liquid in sequentially timed manner to a common channel. It follows that the later one of the first and second channels to transfer liquid to the common channel will itself also receive liquid from the other channel. The one channel accordingly receives two opposite flows which merge. After such merging it is normally appropriate for liquid flow to continue through the one channel in the same direction as the initial flow therein. However, continuing flow from the other channel can act undesirably against this result.

SUMMARY OF THE INVENTION

An object of the present invention is to improve this last situation and to this end the invention provides a device of the above-mentioned more particular form in which the first and second channels interconnect and then both continue. Such an arrangement of channels can be equated with an electrical bridge circuit and, as such, conformed to produce a substantially predetermined flow condition through the channel interconnection. One such condition of particular practical interest is that of null flow.

BRIEF DESCRIPTION OF THE DRAWINGS

The invention is further described below, by way of example, with reference to the accompanying drawings, in which:

FIGS. 1a, 1b, 1c, 1d, 1e, 1f, 1g, 1h, 2a, 2b, 2c, 3a, 3b, 4a, 4b, 4c, 5a, 5b and 5c respectively illustrate different forms of device which accord with the invention and/or are explanatory of the operation of such a device.

DETAILED DESCRIPTION

The device of FIG. 1 is of generally rectangular sheet overall form, denoted at 10, and is respectively illustrated front, rear and side views at (a), (b) and (c).

The device has four pairs of first channels 11 and second channels 12 respectively formed by front and rear layers of porous material, which layers are separated by a liquid impervious membrane 13.

The first channels 11 commence from one end of the device a common portion 11a of narrowed tortuous form. Thereafter the channels assume a broadened rectilinear form having successive portions 11b,c and d. The portion 11b has partway therealong a liquid impermeable bar 14 extending transversely across its central region and portion 11c has three uniformly spaced, parallel, liquid impermeable bars 15 extending therealong define four discrete first channel portions. Each of these last portions has located successively therealong two reagent regions R2 and R1 and a sample application region S.

The membrane 13 is in two portions 13a and b. The first portion 13a extends against first channel portions 11a,b and c up to a point beyond reagent zones R2, but not as far as reagent zones R1. The second membrane portion 13b extends against first channel portions 11c and d from a point just before reagent zones R1 in the former, but without engaging the first membrane portion. There is accordingly a transverse gap 16 between the membrane portions.

The second channels 12 commence from the same end of the device as the first channels in a common portion 12a of narrowed rectilinear form. Thereafter the channels assume a broadened rectilinear form having successive portions 12b and c. These last portions are similar to the first channel portions 11b and c and have respective bars 17 and 18. However, the discrete second channel portions 12c terminate at the gap 16 where they respectively engage the first channel portions 11c.

It will be noted that, as shown, the first channel portion 11d can effectively continue into a portion 11e formed as a part-layer on the other face of the device, with the portions 11a and e being mutually engaged beyond the end of membrane portion 13b.

In practical construction the porous material is suitably of filter paper such as Millipore AP25, and the bars within this material are formed by excision to form slots or by impregnation of wax or other liquid impermeable material. The membrane portions are of any suitable sheet plastics material bonded by adhesive with the porous material. The porous material layers are also bonded together, where they engage at gap 16, and between portions 11a and e, but in such a way as to allow liquid communication by capillary action.

The reagent regions R1 and R2 each contain lyophilised reagent materials impregnated into the porous material. For a typical immunoassay, R1 would be an enzyme-labelled antibody, and R2 a colorimetric substrate. The sample region S would incorporate antibodies, to the antigen of interest in the sample, immobillsed onto the porous material. Each discrete channel may contain similar or different reagents and be related to similar or different samples.

In a typical use of the device, a biological sample, such as serum or urine, is applied to the sample regions S and antigert in the sample begins to bind to the immobilised antibody. The lower end of the device is then immersed into liquid 19 and this flows up the first and second channels as shown by FIG. 1(d). Flow through the first channel portion 11a will take longer than that through the second channel portion 12a because of the tortuous form of the former. In the channel portions 11b and 12b liquid flow is similarly deflected around the respective bars 14 and 17 so as to arrive at the associated discrete channel portions 11c and 12c uniformly in each layer. Liquid flow in the second channels will reach the gap 16 first and passes into the first channels to continue upwardly and downwardly in the latter.

When this upward flow reaches region R1 the associated reagents are reconstituted and carried along with the upward flow. Also the downward flow proceeds to meet the initial upward flow in the first channels, these flows saturate the channels when they meet and then continue as an upward flow carrying along the reconstituted reagents from regions R2. These reagent movements are indicated by FIG. 1(e).

Reagent R1 reaches the sample region S and a portion binds to the immobilised sample. The time between this binding and the earlier application of the sample to the region S allows the sample to incubate. Unbound material is washed away from region S by the continuing upward liquid flow. This phase of operation is indicated by FIG. 1(f).

Further flow then causes reagent R2 to flow through and react with that portion of reagent R1 bound at the sample region as indicated by FIG. 1(g). An insoluble colour is produced, the intensity of which depends upon the amount of the antigen of interest in the sample.

Flow then continues through the sample region, which stabilises the colour, and into the first channel portions 11d and e which serve as a waste reservoir. Flow stops when this reservoir is saturated and the operation is complete. This final phase is indicated by FIG. 1(h).

While there is reference above to first channel portions 11c,d and e, it will be appreciated that beyond the gap 16, where the first and second channels are in liquid flow communication, the portions are common to both channels.

In any event, the device of FIG. 1 is of a beneficially compacted form by virtue of this inter-channel flow communication being effected between superposed layers of porous material in which the discrete first and second channel portions of a multiple device can be respectively formed.

However, the specific form of FIG. 1 can be improved. A significant facet of the operational procedure is the separation of application of the two reagents at the sample region. The extent of this separation is determined, at least in part, by the width of the second channel portion 12a because this determines the volume flow rate of liquid through the second channels. If this flow rate is too large relative to that in the first channels, the former flow will be dominant at the gap 16 and the reagents R2 will move too slowly. If, in compensation, portion 12a is unduly narrowed, the time taken to saturate region 16 can be unacceptably long. This difficulty can be avoided by use of a channel arrangement analogous to a balanced electrical bridge circuit as explained with reference to FIG. 2.

FIG. 2(a) shows a planar device denoted generally at 20 and involving a single pair of first and second channels formed by a single layer of porous material. In comparison with FIG. 1 it will be seen that the planar device has a first channel 21 which starts from one end in a tortuous manner, and then proceeds rectilinearly along the device to its other end where it turns transversely and downwardly into a widened reservoir area 22. In its rectilinear part this channel has reagent and sample regions R1,R2 and S. A second channel 23 of rectilinear form starts from the same end as the first channel and passes in separated manner alongside the latter, except for a transverse interconnection 24 with the first channel between regions R1 and R2, and another 25 at the other end of the device. At the interconnection 24 the on-going second channel changes in width, by widening as shown, in order to modify the on-going resistance to flow relative to that in the preceding channel portion. The relevance of this will be appreciated further below.

Operation of this device will be largely evident from that given above for FIG. 1. Sample is applied to region S and the lower ends of the channels immersed in liquid. Upward liquid flow occurs, but with a delay in the tortuous first channel portion, whereby flow occurs from the second channel, through connection 24, into the first channel. As before, reagents R1 and R2 are reconstituted and carried to the sample S in sequence, with waste products continuing to the reservoir 22.

A difference in this case is that the second channel flow additionally continues separately beyond connection 24 to pass through connection 25 to the waste reservoir.

Now hydraulic flow and pressure are analogous to electrical current and voltage, with hydraulic resistance to flow equating with electrical resistance. The hydraulic situation FIG. 2(a) can then be equated with a Wheatstone bridge circuit with the two channels representing the two sides of the bridge, and the connection 24 representing the cross connection in the bridge circuit. More specifically, the hydraulic resistances in the two channels up to and then beyond connection 24, represent the electrical resistances of the four arms of the bridge circuit and, when these resistances have the same proportions about the cross connection, there is zero flow across this connection. This is desirable for operation of the device of FIG. 2(a) that flow from the second channel cannot dominate that in the first channel following saturation below the connection 25.

FIG. 2(b) illustrates a simplification in which the first and second channel portions above the connection 24 are not physically separated.

FIG. 2(c) shows a modification of FIG. 2(a) which causes flow direction to change or oscillate across the interconnection between the first and second flow channels. This is useful for automating diagnostic systems in which, for example, a sample 'visits' two analytical sites each sensitive to a specific analyte. Alternatively, a chemical may be made to 'oscillate' between two temperature zones, as in a polymerase chain reaction.

Referring to FIG. 2(c), liquid flows up channels 26 and 27 and approaches chemical R3 from both ends of a transverse interconnection channel C. Meanwhile, the liquid continues into portions downstream of the interconnection channel where reservoirs 28 and 29 are provided in channels 26 and 27 respectively. When liquid flows into the first reservoir, for example 28 in FIG. 2(c), the null flow in channel C is disturbed due to the resulting reduction in flow resistance in channel 26 and R3 is carried to the left along the channel. Subsequently, liquid flows into reservoir 29 in channel 27 and the balance of flow is again changed, moving R3 to the right along channel C. Further reservoirs may be added in series (not shown) to increase the number of cycles in this flow oscillation.

FIG. 3 illustrates devices similar to those of FIG. 2 in being of planar form from a single layer of porous material, but in this case they are also of multiple form involving plural pairs of channels.

The device of FIG. 3(a) is denoted generally at 30. It has first channels 31 of similar form to those of FIG. 1 in having a tortuous portion connected to a rectilinear portion which first has a transverse deflector bar 32 and then longitudinal channel separator bars 33. Thereafter the first channels rejoin in a common portion which is transversely necked in, as discussed below, and broadened again into a further portion with longitudinal channel separator bars 34.

The second channels 35 are deployed on both sides of the first channel array in an effective duplication of the unilateral arrangement in FIG. 2(a), with cross connections 36 to the first channels intermediate reagent regions R1 and R2. These connections are defined by transverse channel separating bars 37 projecting from those which separate the first and second channels longitudinally. The bars 37 are of lengths such as to cause flow from the second channels to progress into the first channels, upwardly and downwardly, in a uniform manner.

Operation of this device will be evident from that described above for FIGS. 1 and 2. However, it is to be noted that when the cross connections 36 and the preceding channel portions are saturated, there is to be zero flow in the connections. In these circumstances reagents R2 are carried upwardly through the necked first channel portions, along curved streambands, and there is a tendency for the reagents to become diffuse as these bands become longer.

FIG. 3(b) shows this last device modified in similar manner as FIG. 2(b) relative to 2(a) by omission of the upper first and second channel separating bars and, in addition, the cross connection bars 37. At the same time the gap at connections 36 between the upper and lower channel portions is narrowed and the flow deflector bar 32 is widened. In the result the opposite flows towards reagents R2 have similar circular wavefronts indicated at 38 which will meet to form, at saturation, a temporary stagnation line 39 of generally rectilinear form across the device. The reconstituted reagents R2 will then move from this line uniformly upwards with no significant risk of diffusion.

The bridge-like forms described above need to be fully wetted in order to balance effectively. The device 40 of FIG. 4 is modified relative to that of FIG. 3 to facilitate this result.

FIG. 4 in fact involves two layers of porous material, somewhat like FIG. 1, and so is shown in front, rear and side views respectively at (a), (b) and (c).

The front layer has a form corresponding to FIG. 3(b) except for two additions.

The first addition involves the provision of two reservoirs 41 connected at 42 with the opposite sides of the first channel common portion which incorporates the transverse deflector bar 43. These reservoirs delay movement of reagent R2 during saturation of the bridge from below, particularly in relation to the relatively modest flow contributions from the second channels, and ensure uniformity of flow across the thickness of the porous material, which otherwise may tend to saturate at different rates on opposite surfaces. The extent of the time delay depends on the area of the reservoirs 41 and the size of the connections 42.

The second addition involves the provision of two further deflector bars 44 above the uppermost ends of the discrete first channels. These bars serve to apply flow uniformly to the channels in a downward direction and avoid a need for these channels to be unduly narrow.

This last flow is provided by the rear layer 45 which is of T-shape to convey liquid up to and across the front layer behind the deflector bars 44. This flow serves to ensure adequate saturation of the bridge from above.

The rear layer can also provide a separate portion to connect at the top of the device with the waste reservoir and so further compact the device as in FIG. 1.

Turning lastly to the device of FIG. 5, this is a modification of that of FIG. 1 but which employs the benefits of a bridge.

As with FIG. 1, the device of FIG. 5 Is shown in front, rear and side views respectively at (a), (b) and (c). FIG. 5 in fact shows one difference, namely, that the waste reservoir does not continue from the front layer to the rear, but Instead the second channels at the rear continue upwardly, after transverse engagement 16 with the first channels, into a common portion. The result, as seen In side view, is to form an effective bridge whereby, at saturation above, there is no flow between the first and second channels.

What is claimed is:

1. A device for performing biochemical diagnostic assays, comprising:

first, second, third and fourth liquid flow channels of porous material;

the first and second channels leading from a respective pair of channel ends and interconnecting at a common site, said first and second channels being operable to transfer liquid by capillary flow to the common site in sequentially timed manner following simultaneous application of the liquid to the pair of channel ends, arrival of flow at the common site from the second channel being delayed relative to that from the first channel;

said third and fourth channels leading from the common site to provide, respectively, ongoing flow paths for liquid flow from the first channel to the third channel and from the second channel to the fourth channel from the common site;

a sample binding site provided in said fourth channel, said sample binding site having an analyte binding reagent fixed thereto;

a first reagent releasably bound to said fourth flow channel between said common site and said sample binding site; and a second reagent releasably bound to said second flow channel.

2. A device for performing biochemical diagnostic assays, comprising:

first, second, third and fourth liquid flow channels of porous material;

the first and second channels leading from a respective pair of channel ends and interconnecting at a common site, said first and second channels being operable to transfer liquid by capillary flow to the common site in sequentially timed manner following simultaneous application of the liquid to the pair of channel ends;

said third and fourth channels leading from the common site to provide, respectively, ongoing flow paths for liquid flow from the first channel to the third channel and from the second channel to the fourth channel from the common site;

said channels producing substantially null net flow across the common site when said first and second channels are saturated at least as far as the common site, thereby preventing net flow between, on the one hand, said first and third channels, and, on the other hand, said second and fourth channels.

3. A device according to claim 2, wherein the channels have hydraulic resistances selected to provide said null flow condition.

4. A device according to claim 3, wherein the channels have cross sectional dimensions selected to provide said null flow condition.

5. A device according to claim 1 or 2, wherein said first channel and said second channel each comprise respectively separate portions, as do said third channel and said fourth channel.

6. A device according to claim 5, wherein the ratio of the hydraulic resistance in the flow direction of the first channel to that of the third channel is substantially equal to the ratio of the hydraulic resistance, in the flow direction, of the second channel to that of the fourth channel.

7. A device according to claim 5, wherein at least one of the third channel and fourth channels comprise zones of varying hydraulic resistance in the flow direction.

8. A device according to claim 7, wherein the zones of varying hydraulic resistance are arranged to produce oscillating flow across the common site between the first and second channels.

9. A device according to claim 1 or 2, wherein at least one of the channels has a plurality of sub-channels arranged in parallel.

10. A device according to claim 9, wherein each of said sub-channels has first and second ends, and at least one transverse flow obstacle is provided adjacent to at least one of the first and second ends of said sub-channels.

11. A device according to claim 10, wherein one of said transverse flow obstacles is provided for every two said sub-channels.

12. A device according to claim 1 or 2, wherein the channels comprise superposed layers of porous materials separated by an impervious layer being omitted at the common site between said first and second channels.

13. A device according to claim 1 or 2, wherein device comprises a single sheet of porous material and said channels are formed by providing impervious flow separating zones within said sheet.

14. A device according to claim 13, wherein one of said first and said second channels extends from said channel ends towards said common site in a portion disposed generally centrally of said sheet, and the other of said first and second channels extends from said one end towards said common site extending in two side portions opposed about said central portion, said central portion and said side portions providing liquid flow from said one end to said common site in sequentially time manner, wherein said side portions interconnect with said one channel in two zones transverse to said side portions and said side portions have downstream portions to provide ongoing flow paths beyond said common site.

15. A device according to claim 14, wherein flows of liquid from the first and second channels meet in a substantially straight intersection front.

16. A device according to claim 1 or 2, wherein a further liquid flow channel is provided interconnecting with at least one of said first, second, third and fourth channels, said further channel being located such that liquid can be applied simultaneously to the channel ends of said first and second channels and said further channel.

17. A device according to claims 1 or 2, wherein a flow delay reservoir is provided in at least one of said first and second channels.

* * * * *